US00PP08471P

United States Patent [19]

Zaiger et al.

[11] Patent Number: Plant 8,471

[45] Date of Patent: Nov. 23, 1993

[54] PLUM TREE "BETTY ANNE"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 8,983

[22] Filed: Jan. 25, 1993

[51] Int. Cl.[5] ..... A01H 5/00

[52] U.S. Cl. ..... Plt./38.1

[58] Field of Search ..... Plt./38.1

*Primary Examiner*—James R. Feyrer

[57] ABSTRACT

A new and distinct variety of plum tree; its novelty consisting of the following unique combination of features that are outstanding in a new variety.

1. Heavy and regular bearing of large fruit.
2. Late maturity of fruit.
3. Fruit that will hold firm on the tree 12 to 15 days after shipping ripe.
4. Fruit with good handling and shipping quality.
5. Fruit with good flavor and eating quality.
6. Vigorous, upright tree growth.
7. Relatively uniform ripening of fruit throughout the tree.

1 Drawing Sheet

ORIGIN OF THE VARIETY

The present new variety of plum tree was originated by us in our experimental orchard located near Modesto, Calif., as a first generation cross between a selected seedling with the field identification number 105GD271 and Autumn Giant Plum (U.S. Plant Pat. No. 5,624). The maternal parent with the field identification number 105GD271 originated from a cross between Friar Plum (non-patented) and a selected seedling labeled 59GA511. The selected seedling 59GA511 originated from a cross between Mariposa Plum (U.S. Plant Pat. No. 111) and Ebony Plum (U.S. Plant Pat. No. 2,049). We grew and maintained a large number of these first generation seedlings which gave many and varying characteristics, one such seedling, which is the present variety, exhibited distinct and desirable fruit characteristics was selected for asexual reproduction and commercialization.

ASEXUAL REPRODUCTION OF THE VARIETY

The present new variety of plum tree was asexually reproduced by budding, as performed by us in our experimental orchard located near Modesto, Calif. and shows that all characteristics of the tree and its fruit run true to the original tree and are established and transmitted through succeeding propagations.

SUMMARY OF THE VARIETY

The new and distinct variety of plum tree is of large size, vigorous upright growth and a productive and regular bearer of large, firm, clingstone fruit with good flavor and eating quality and ripening in the late maturity season. The fruit is further characterized by holding firm on the tree 12 to 15 days after maturity (shipping ripe) with good handling, storage, shipping quality and having an attractive red skin color. In comparison to the Autumn Giant Plum (U.S. Plant Pat. No. 5,624), with which it has certain characteristics in common, the new variety has firmer flesh and can tolerate hotter growing temperatures without internal flesh breakdown within the fruit.

BRIEF DESCRIPTION OF THE PHOTOGRAPHS

The accompanying photographs show reproductions in color of typical specimens of the foliage and fruit of our new variety. The upper and lower surface of the leaves being shown, an exterior and sectional view of the fruit being divided in the suture plane to reveal flesh coloration, pit cavity and showing a stone remaining in place. The illustrations were taken shortly after being picked at maturity (firm ripe) and the colors are as nearly true as reasonably possible in a color representation of this type.

DESCRIPTION OF THE VARIETY

The following is a detailed botanical description of the new variety of plum tree, its flowers, foliage and fruit based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Productive.
- *Bearing.*—Regular bearer.

Trunk:
- *Size.*—Medium to stocky.
- *Texture.*—Medium shaggy.
- *Color.*—Dull brown to brown (6-E-5) to (6-F-5).

Branches:
- *Size.*—Medium.
- *Surface.*—Medium rough.
- *Lenticeis.*—Medium number. Medium size.
- *Color.*—Light brown to brown.

Leaves:
- *Size.*—Medium. Average length — 4¼". Average width — 1½".
- *Texture.*—Smooth.
- *Thickness.*—Medium.
- *Form.*—Oblanceolate. Pointed.
- *Margin.*—Serrulate.
- *Petiole.*—Medium length. Medium thickness.
- *Glands.*—Globose. Number varies from 0 to 4. Average number 1.

*Color.*—Upper surface — light green to green (26-E-5) to (26-E-7). Lower surface — dull green to grayish green (25-D-4) to (25-D-6).

Flower buds:

*Size.*—Medium.

*Length.*—Medium.

*Shape.*—Plump.

Flowers:

*Blooming period.*—Mar. 1, 1992 to Mar. 8, 1992. Varies slightly with climatic conditions.

*Size.*—Medium.

*Pollen.*—Present.

*Color.*—White.

Fruit:

*Maturity when described.*—Firm ripe.

*Date of first picking.*—Aug. 24, 1992.

*Date of last picking.*—Sep. 2, 1992.

*Size.*—Large. Average diameter axially — 2¼" to 2½". Average transversely in suture plane — 2¼" to 2½".

*Form.*—Nearly Globose — slightly flattened at base and on suture side.

*Suture.*—Pronounced — extends from base to apex.

*Ventral surface.*—Varies from round to slightly recessed, lipped.

*Base.*—Retuse.

*Cavity.*—Rounded. Average depth — ¼". Average breadth — ½".

Flesh:

*Texture.*—Firm and meaty.

*Fibers.*—Small, few, tender.

*Ripens.*—Evenly.

*Flavor.*—Mild — good balance between acid and sugar.

*Eating quality.*—Good.

*Juice.*—Moderate.

*Color.*—Varies from yellow white to pinkish white (6-A-2) to (7-A-2) as distance from pit cavity increases toward skin surface. Pit cavity — dull reddish brown (8-B-5) to (8-B-6), surface color stained from stone.

Skin:

*Thickness.*—Medium.

*Texture.*—Medium, tenacious to flesh.

*Tendency to crack.*—Very slight.

*Down.*—Wanting.

*Bloom.*—Moderate.

*Color.*—Pale yellow to cream yellow ground color (4-A-2) to (4-A-4). Overspread with red to madder red (10-B-8) to (11-B-8). Numerous small dots of yellow ground color.

Stone:

*Type.*—Clingstone.

*Size.*—Small to medium. Average length. — 1". Average width. — ¾". Average thickness. — ½".

*Form.*—Ovoid

*Sides.*—Mostly equal — some unequal.

*Surface.*—Very shallow furrows, deeper toward base, lightly pitted throughout.

*Base.*—Straight, width of base varies slightly.

*Apex.*—Acuminate.

*Tendency to split.*—None.

*Color.*—Varies from light brown to brown (8-D-4) to (8-D-7).

Use: Dessert.

*Market.*—Local and long distance.

Storage quality: Good.

Shipping quality: Good.

The present new variety of plum tree, is flowers, foliage and fruit may vary in slight detail due to climatic, soil conditions and cultural practices under which the variety may be grown; the present botanical description is that of the variety grown under the ecological conditions prevailing near Modesto, Calif.

We claim:

1. A new and distinct variety of plum tree, substantially as illustrated and described, characterized by its large size, vigorous upright growth and a productive and regular bearer of large, firm, clingstone fruit with good flavor and eating quality; the fruit is further characterized by having an attractive red skin color, having good storage and shipping quality and in comparison to Autumn Giant Plum (U.S. Plant Pat. No. 5,624), has firmer flesh with no internal flesh breakdown during growing periods of high temperatures.

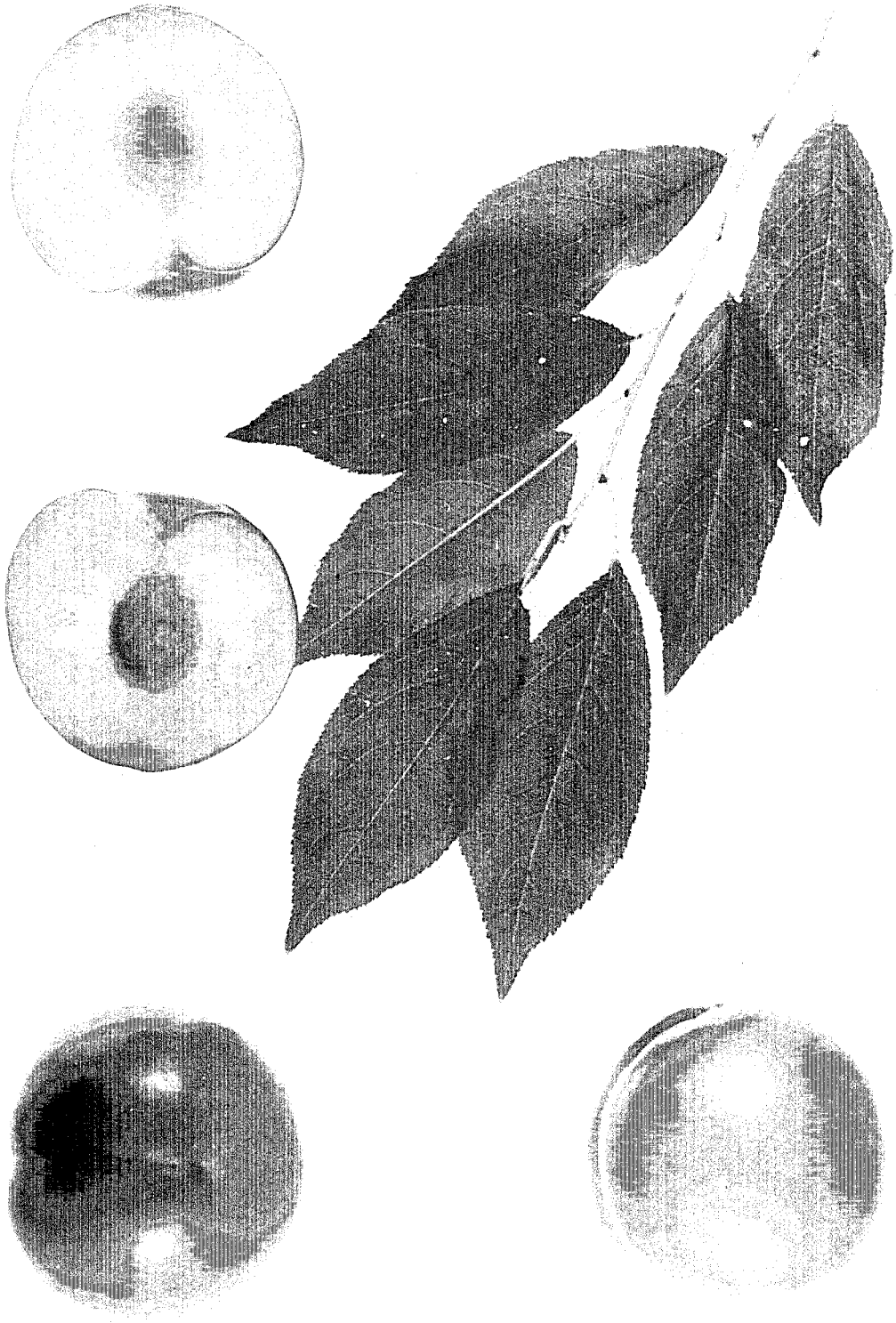

* * * * *